United States Patent [19]

Cella et al.

[11] 4,238,401

[45] Dec. 9, 1980

[54] ALKOXYSILICON MATERIALS AND METHOD FOR MAKING

[75] Inventors: James A. Cella, Clifton Park; Tyrone D. Mitchell, Albany, both of N.Y.

[73] Assignee: General Electric Company, Schenectady, N.Y.

[21] Appl. No.: 927,287

[22] Filed: Jul. 24, 1978

[51] Int. Cl.$^3$ ............................................... C07F 7/18
[52] U.S. Cl. ............................. 556/436; 260/326.61; 260/347.8; 260/345.2; 260/345.9 R; 260/239.95; 260/239 B; 260/239 BC; 260/239.3 R; 260/239.3 A; 260/326.5 R; 260/326.5 C; 546/14; 544/69; 544/3; 544/5; 544/7; 544/229
[58] Field of Search ................... 260/448.8 R, 326.61, 260/347.8, 345.2, 345.9 R; 544/69; 546/14

[56] References Cited

PUBLICATIONS

Torkelson et al., "Synthesis", pp. 722–724, 1976.
Hengge et al., "Monatschift Für Chemie", 104, pp. 1071–1076, 1973.

*Primary Examiner*—Paul F. Shaver
*Attorney, Agent, or Firm*—William A. Teoli; James C. Davis, Jr.

[57] ABSTRACT

Alkoxysilyl ethers of 1,3-dicarbonyl cyclic compounds, such as methoxy tris-5,5-dimethyl-cyclohexen-2-one-3-yloxy silane can be made by effecting reaction in the presence of an acid acceptor between an alkanol, a halosilane and a 1,3-dicarbonyl cyclic organic compound, for example, 5,5-dimethyl-1,3-cyclohexane dione. The alkoxysilyl ethers are useful as vulcanizing agents for silanol terminated polydiorganosiloxanes.

6 Claims, No Drawings

ALKOXYSILICON MATERIALS AND METHOD FOR MAKING

BACKGROUND OF THE INVENTION

The present invention relates to certain alkoxysilyl ethers of 1,3-dicarbonyl cyclic organic compounds and a method for making such materials.

As shown in copending application Ser. No. 927,288 of James A. Cella, filed July 24, 1978 and assigned to the same assignee as the present invention, silyl ethers of the formula

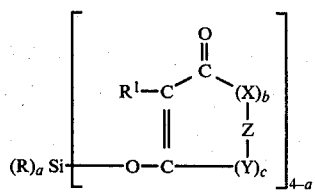

where R is a $C_{(1-13)}$ monovalent organic radical, a has a value of 0 to 2 inclusive and $R^1$, X, Y, Z, b and c are defined below, can be used as curing agents with silanol terminated organopolysiloxanes to produce moisture curable compositions. Experience has shown that the moisture curable compositions made with the above silyl ethers often cure exceptionally fast and reduce the useable worklife of the moisture curable organopolysiloxane compositions. Efforts to extend the cure rate led to the development of silyl ether substituted with R radicals in the form of $C_{(4-12)}$ alkyl radicals. However, the synthesis of such silyl ethers having long chain alkyl radicals is often uneconomical and further limits the utility of such silyl ethers.

STATEMENT OF THE INVENTION

The present invention is based on the discovery that alkoxysilyl ethers having the formula,

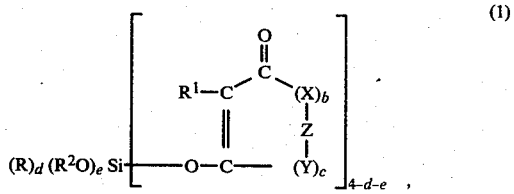

can be used with silanol terminated organopolysiloxanes to produce moisture curable organopolysiloxanes having improved worklife, where R is defined above, $R^1$ is selected from hydrogen, halogen and R, $R^2$ is a $C_{(1-8)}$ alkyl radical, X and Y are divalent radicals selected from —O—, —S—, and

Z is a divalent $C_{(1-13)}$ organic radical selected from alkylene, cycloalkylene, arylene and a fused ring structure, b and c are equal to 0 or 1, $R^3$ is selected from hydrogen and R, d is a whole number having a value of from 0 to 2 inclusive, e is an integer having a value of from 1 to 3 inclusive and the sum of d+E has a value of from 1 to 3 inclusive.

Radicals included by R of formula (1) are aryl radicals and halogenated aryl radicals, such as phenyl, chlorophenyl, xylyl, tolyl, etc.; aralkyl radicals, such as phenylethyl, benzyl, etc.; alkyl and alkenyl radicals, such as methyl, ethyl, propyl, chloromethyl, butyl, vinyl, etc.; cyclo alkyl, such as cyclohexyl, cycloheptyl, etc. Radicals included by $R^2$ are, for example, methyl, ethyl, propyl, butyl, pentyl, hexyl, etc. In formula (1), where R and $R^2$ can represent more than one radical, these radicals can be the same or different.

The alkoxysilyl ethers of formula (1) can be made by effecting reaction under substantially anhydrous conditions between an aliphatic alcohol of the formula, $$R^2OH, \qquad (2)$$

an organohalosilane of the formula, $$(R)_dSiQ_{4-d}, \qquad (3)$$

ps where R, $R^2$ and d are as previously defined and Q is a halogen radical, and a cyclic 1,3-dicarbonyl compound of the formula,

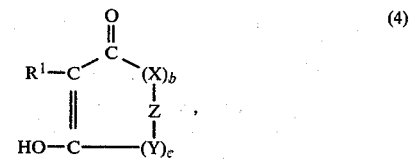

in the presence of a base catalyst where $R^1$, X, Y, Z, b and c are as previously defined.

There are included within the organohalosilanes of formula (3) compounds having the formulas,

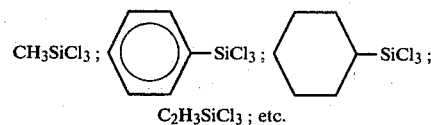

Included within formula (2), are aliphatic alcohols such as:

$CH_3OH$; $(CH_3)_3CCH_2$—OH; $CH_3CH_2OH$;

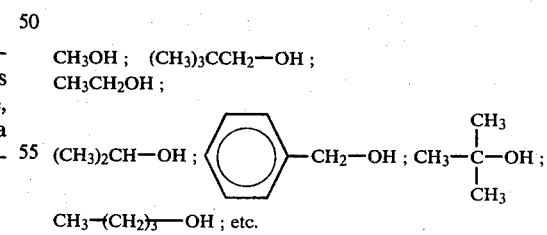

$CH_3$—$(CH_2)_3$—OH; etc.

The cyclic 1,3-dicarbonyl compounds of formula (4) include cyclohexane-1,3-dione, isopropylidene malonate, 3-hydroxycoumrin, 5,5-dimethylcyclohexane-1,3-dione, 2-methylcyclopentane-1,3-dione, 2-bromocyclohexane-1,3-dione, 5,5-dimethyl-3-keto-valerolactone, N-phenyl-3-ketobutyrolactam, etc.

Among the alkoxy silylethers of formula (1) there are included

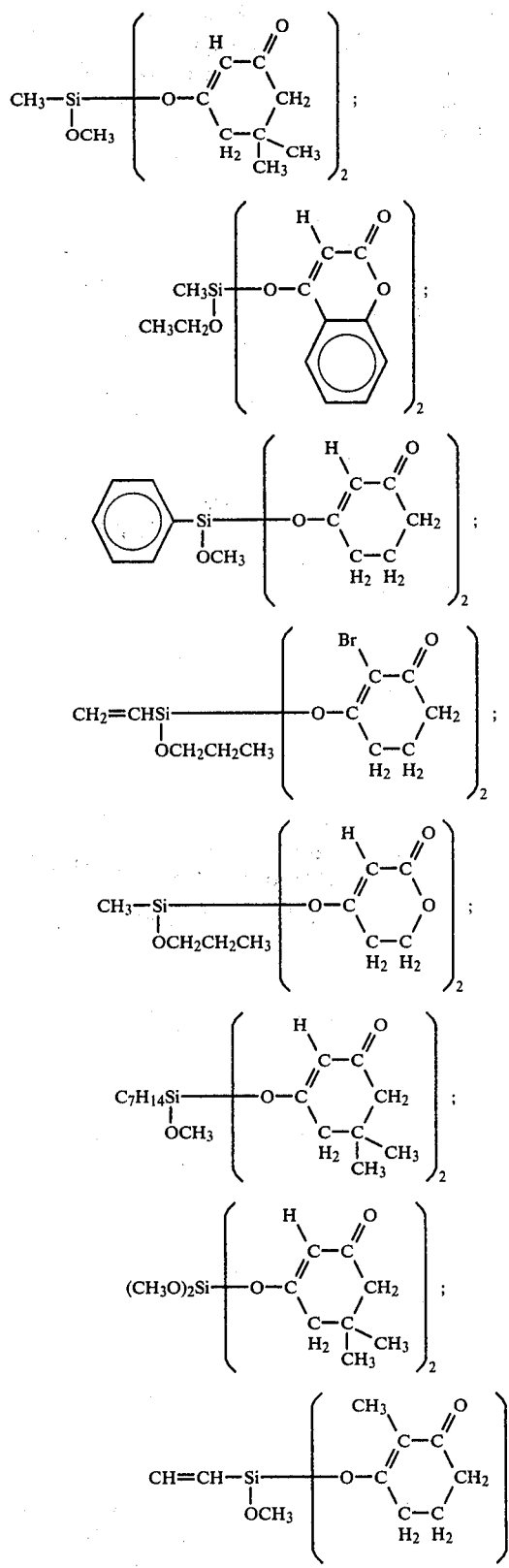

In the practice of the invention, the alkoxy silyl ethers of formula (1) can be made by effecting reaction under substantially anhydrous conditions between 1-4 mols of the 1,3-dione of formula (3), and 1 to 2 moles of the aliphatic alcohol of formula (2), per mole of the organohalosilane of formula (3), to insure that there is at least a stoichiometric equivalent between the gram mols of hydroxy of the 1,3-dione and the aliphatic alcohol and the halogen attached to silicon of the organohalosilane. The order of addition of the various reactants is not critical.

Reaction between the 1,3-dione and aliphatic alcohol and the organosilane is effected in the presence of a basic acceptor, such as organic amine, for example, triethylamine, pyridine, etc. Reaction can be facilitated by use of a nonpolar neutral organic solvent, such as toluene, benzene, hexane, pentane, chloroform, etc., at temperatures in the range of from 0° C. to 150° C. During the reaction, the mixture can be agitated such as by stirring, etc. The mixture then can be filtered of amine salts and the filtrate stripped of organic solvent.

In order that those skilled in the art will be better able to practice the invention, the following examples are given by way of illustration and not by way of limitation. All parts are by weight.

EXAMPLE 1

There was added 21.62 parts of anhydrous methanol to 100 parts of methyltrichlorosilane which was stirring under nitrogen. After hydrogen chloride evolution had ceased, 72.5 parts of the resulting clear solution was added dropwise to a stirred solution of 140 parts of 5,5-dimethyl-1,3-cyclohexanedione, 160 parts of triethylamine and 2400 parts of dry toluene.

The mixture was then filtered to remove triethylamine hydrochloride and the filtrate was stripped of solvent. There was obtained 182 parts of methylmethoxy bis-5,5-dimethylcyclohexane-1-one-3-yloxysilane having the formula,

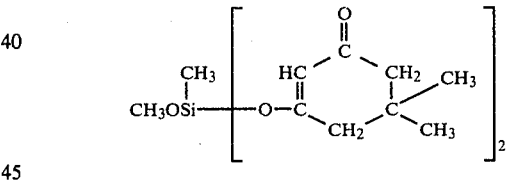

The identity of the 1,3-dicarbonylsilane was confirmed by its NMR spectrum.

A blend of 6 parts of the above 1,3-dicarbonylsilane, 100 parts of silanol terminated polydimethylsiloxane having a viscosity of about 35,000 centipoises at 25° C., 20 parts of fumed silica and 0.06 part of dibutyltindilaurate is mixed under substantially anhydrous conditions. A tack-free substantially odorless elastomer is formed in about one hour. A complete cure is achieved in about 20 hours under atmospheric conditions.

EXAMPLE 2

The procedure of Example 1 was repeated, except that a variety of aliphatic alcohols were used in combination with methyltrichlorosilane and 5,5-dimethyl-1,3-cyclohexanedione to produce a variety of alkoxy-substituted 1,3-dicarbonylsilanes. In instances where methanol was used as the aliphatic alcohol, the proportion of mols of methanol per mol of the methyltrichlorosilane was varied to produce methoxy-substituted silanes having a range of from about 0.3 to 1 mol of methoxy radicals per mol of the resulting 1,3-dicarbonylsilane. In instances where higher aliphatic alcohols were used, up to about 1 mol of alkoxy per mol of silane was used.

Moisture curable mixtures were then prepared following the procedure of Example 1 with each of the above-described alkoxy-substituted 1,3-dicarbonylsilanes to determine the effect of alkoxy-substitution on the terminal siloxy units in the respective polydimethylsiloxane moisture curable formulations and the length of the alkyl radical of the alkoxy radical with respect to the length of time required for forming a skin on the surface of the exposed moisture curable organopolysiloxane compositions or "work life". In addition, the tack-free time of the respective moisture curable organopolysiloxane compositions was also determined. All of the moisture curable organopolysiloxane compositions were examined while in aluminum cups which were exposed to atmospheric conditions. A moisture curable organopolysiloxane composition having terminal siloxy units substituted with 1,3-dicarbonyl silyl ether radicals free of alkoxy radicals was also evaluated.

The following results were obtained where "alcohol" represents the alcohol used in preparing the 1,3-dicarbonylsilane and "mols" represents the mols of alcohol per mol of methyltrichlorosilane utilized:

| Alcohol | Mols | Work Life (min) | Tack-Free Time (min) |
|---|---|---|---|
| — | 0 | 0.5-1.0 | 3-5 |
| methanol | 0.3 | 5 | 3 |
| methanol | 0.5 | 5 | 30 |
| methanol | 1.0 | — | 40 |
| ethanol | 1.0 | 60-120 | — |
| propanol | 1.0 | " | — |
| isopropanol | 1.0 | " | — |

The above results show that 1,3-dicarbonylsilanes substituted with alkoxy radicals are capable of extending the work life of moisture curable organopolysiloxane compositions as compared to 1,3-dicarbonylsilanes free of alkoxy radicals. In addition, the length of the alkyl groups on the aliphatic alcohol also influences the cure characteristics of the resulting moisture curable organopolysiloxane composition having terminal alkoxy substituted siloxy units.

EXAMPLE 3

In accordance with the procedure of Example 1, a mixture of 31.1 parts of ethanol, 100 parts of methyltrichlorosilane, 190.4 parts of 5,5-dimethyl-1,3-cyclohexanedione, 141.4 parts of triethylamine and about 3,000 parts of toluene was employed to produce an ethoxy 1,3-dicarbonylsilane having the formula,

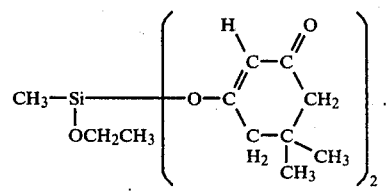

The above ethoxy-substituted silane was utilized with a silanol-terminated polydimethylsiloxane in accordance with Example 1 and there was obtained a moisture curable organopolysiloxane composition convertible to the solid elastomeric state upon exposure under atmospheric conditions.

Although the above examples are directed to only a few of the very many variables in the practice of the method of the present invention, it should be understood that the method of the present invention is further described in the description preceding such examples as shown by the use of an aliphatic alcohol of formula (1), an organohalosilane of formula (3) and a cyclic 1,3-dicarbonyl compound of formula (4). In addition, alkoxy silyl ethers provided by the present invention are included within formula (1). Moisture curable organopolysiloxanes based on the use of silyl ethers of copending application Ser. No. 927,288 of James A. Cella are shown in copending application Ser. No. 927,286, now U.S. Pat. No. 4,176,111 of James A. Cella, filed July 24, 1978.

What we claim as new and desire to secure by Letters Patent of the United States is:

1. The compound

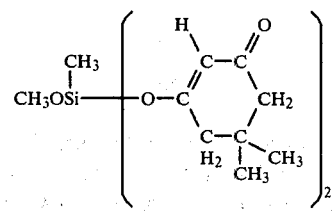

2. The compound

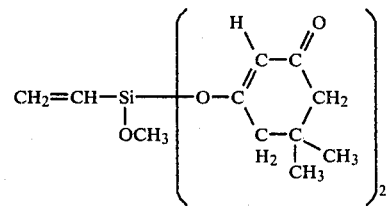

3. The compound

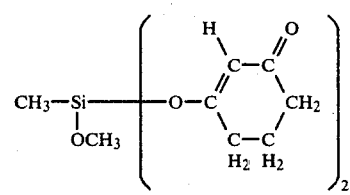

4. The compound

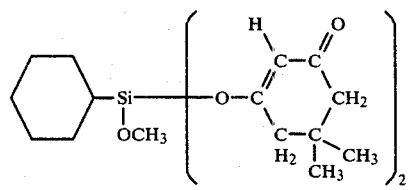

5. A method for making an alkoxy-substituted 1,3-dicarbonylsilyl ether which comprises
   (1) effecting reaction between an aliphatic alcohol, an organohalosilane of the formula, $(R)_a SiQ_{4-a}$ and a 1,3-dione of the formula,

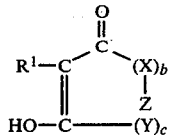

in the presence of an acid acceptor and (2) recovering the resulting alkoxy-substituted 1,3-dicarbonylsilyl ether from step (1), where R is a $C_{(1-13)}$ monovalent organic radical, $R^1$ is selected from hydrogen, halogen and R, X and Y are divalent radicals selected from —O—, —S—, and

Z is a divalent $C_{(1-13)}$ organic radical selected from alkylene, cycloalkylene, arylene and a fused ring structure, a is a whole number having a value of from 0 to 2 inclusive, b and c are equal to 0 or 1, $R^3$ is selected from hydrogen and R radicals, Q is a halogen radical.

6. 1,3-silyl carbonyl ethers of the formula,

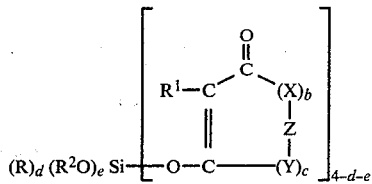

where R is a $C_{(1-13)}$ monovalent organic radical, $R^1$ is selected from hydrogen, halogen and R, $R^2$ is a $C_{(1-8)}$ alkyl radical, X and Y are divalent radicals selected from —O—, —S— and

Z is a divalent $C_{(1-13)}$ organic radical selected from alkylene, cycloalkylene, arylene and a fused ring structure, b and c are equal to 0 or 1, $R^3$ is selected from hydrogen and R, d is a whole number having a value of from 0 to 2 inclusive, e is a whole number having a value of from 1 to 3 inclusive and the sum of d+e has a value of from 1 to 3 inclusive.

* * * * *